United States Patent [19]
Valdivia et al.

[11] Patent Number: 5,994,077
[45] Date of Patent: Nov. 30, 1999

[54] FLOURESCENCE-BASED ISOLATION OF DIFFERENTIALLY INDUCED GENES

[75] Inventors: Raphael H. Valdivia, Palo Alto; Brendan P. Cormack, Santa Cruz; Stanley Falkow, Portola Valley, all of Calif.

[73] Assignee: The Board of Trustees of the Leland Stanford Junior University, Palo Alto, Calif.

[21] Appl. No.: 08/926,556

[22] Filed: Sep. 10, 1997

Related U.S. Application Data

[63] Continuation-in-part of application No. 08/791,332, Jan. 31, 1997, Pat. No. 5,804,387.

[51] Int. Cl.[6] .............................. C12Q 1/68; C12P 21/06; C12P 21/04; C12N 9/02
[52] U.S. Cl. ........................ 435/6; 435/69.1; 435/189; 435/69.7; 435/252.3; 536/23.1; 536/23.4; 536/23.5; 536/22.1
[58] Field of Search .................................. 435/69.1, 189, 435/6, 69.7, 252.3; 536/23.4, 23.5, 22.1, 23.1

[56] References Cited

U.S. PATENT DOCUMENTS

| | | | |
|---|---|---|---|
| 5,491,084 | 2/1996 | Chalfie et al. | 435/189 |
| 5,625,048 | 4/1997 | Tsien et al. | 536/23.4 |

OTHER PUBLICATIONS

Mahan, M. et al., *Selection of Bacterial Virulence Genes That Are Specifically Induced in Host Tissues*, Science, vol. 259, Jan. 29, 1993, pp. 686–688.

Baringa, M., *New Technique Offers a Window on Bacteria's Secret Weapon's*, Science, vol. 259, Jan. 29, 1993, p. 595.

Heithoff, D. et al., *Bacterial infection as assessed by in vivo gene expression*, Proc. Natl. Acad. Sci. USA, vol. 94, pp. 934–939, Feb. 1997.

Mahan, M. et al., *Antibiotic–based selection for bacterial genes that are specifically induced during infection in host*, Proc. Natl. Acad. Sci. USA, vol. 92, pp. 669–673, Jan. 1995.

Sambrook, et al. : Molecular Cloning a laboratory manual second edition: pp. 12.2–12.44, 1989.

Mahan, et al. : Antibiotic–based selection for bacterial genes...: Proc. Natl. Acad. Sci.: vol. 92: pp. 669–673, Jan. 1995.

*Primary Examiner*—Frank C. Eisenchenk
*Assistant Examiner*—Brett Nelson
*Attorney, Agent, or Firm*—Bozicevic, Field & Francis LLP; Pamela Sherwood

[57] ABSTRACT

Regulatory elements (e.g. promoters) activated by a stimulus are isolated by a FACS-based method. Preferably, a library of random fragments representative of a target (e.g. bacterial) genome are cloned in front of a promoterless gfp (green fluorescent protein) sequence in a plasmid, and inserted into target cells. The resulting target cell mixture is sorted according to GFP levels in the presence and the absence of the stimulus. Suitable stimuli include compounds of interest (e.g. drugs), environmental factors (e.g. extracellular acidity), and complex stimuli such as in vivo environments of hosts infected by the target cells. The method allows identifying pathogen genes which are selectively expressed during infection.

15 Claims, 6 Drawing Sheets

2A
2B
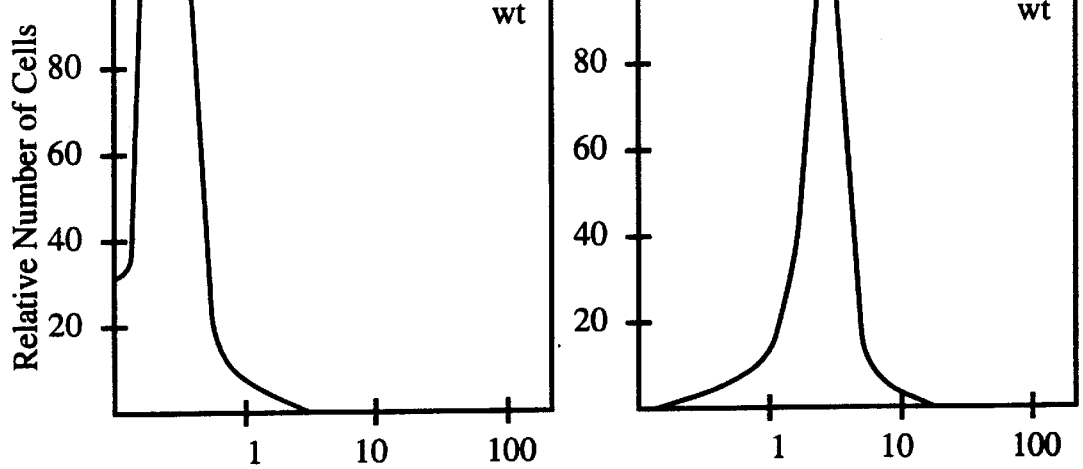
2C
2D
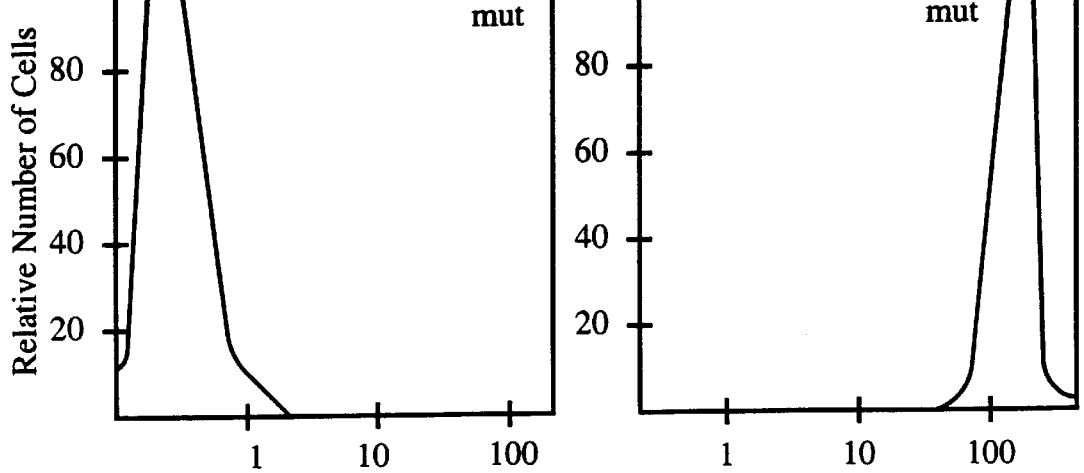
Fluorescence Intensity (log scale) with 488 nm excitation
Emission read with 510/40 bandpass filter
FIG. 2

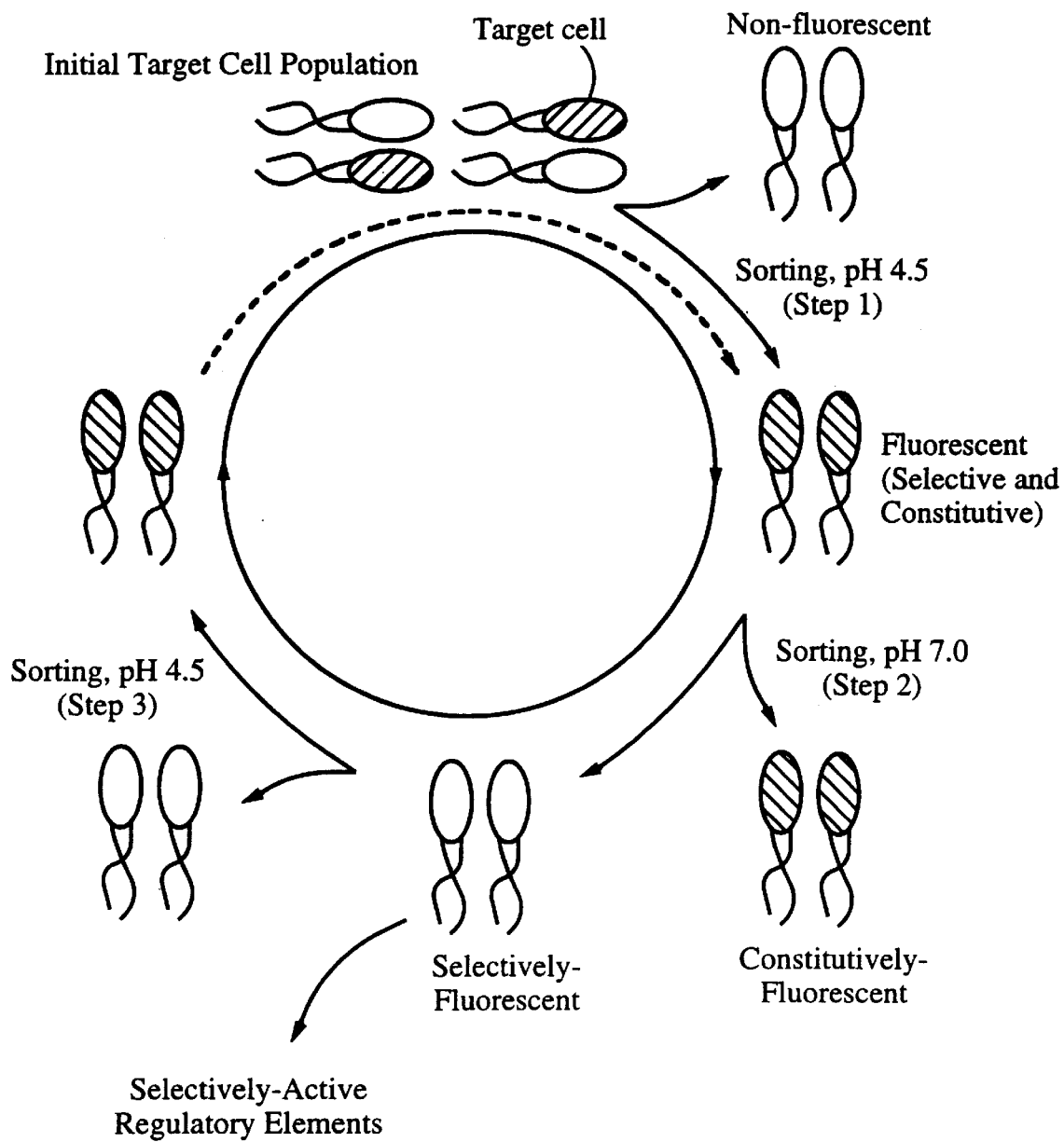
FIG. 3-A

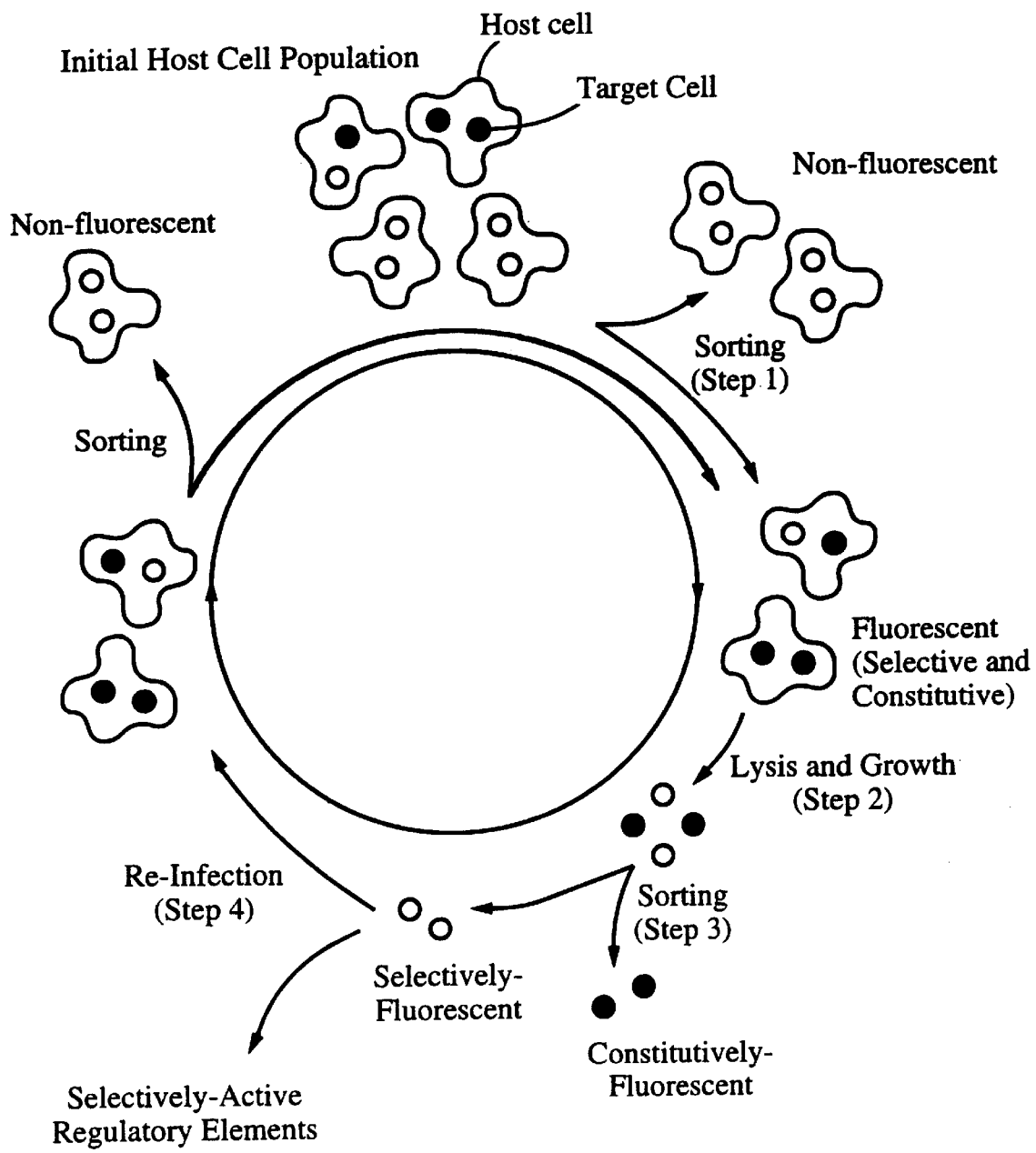
FIG. 3-B

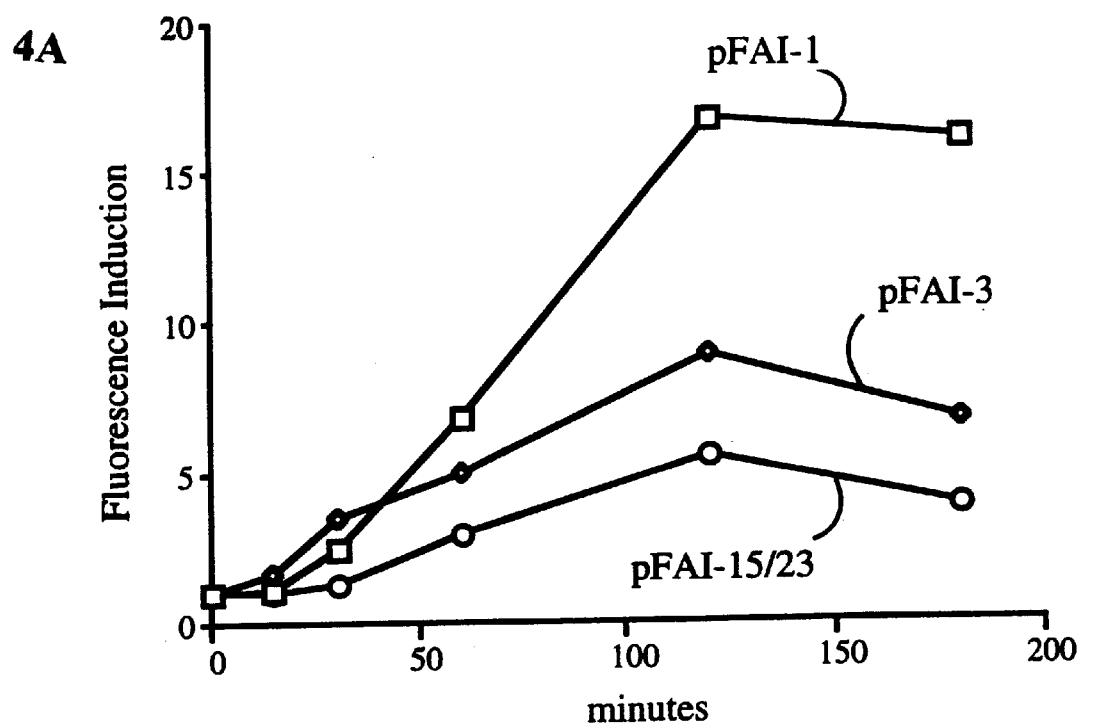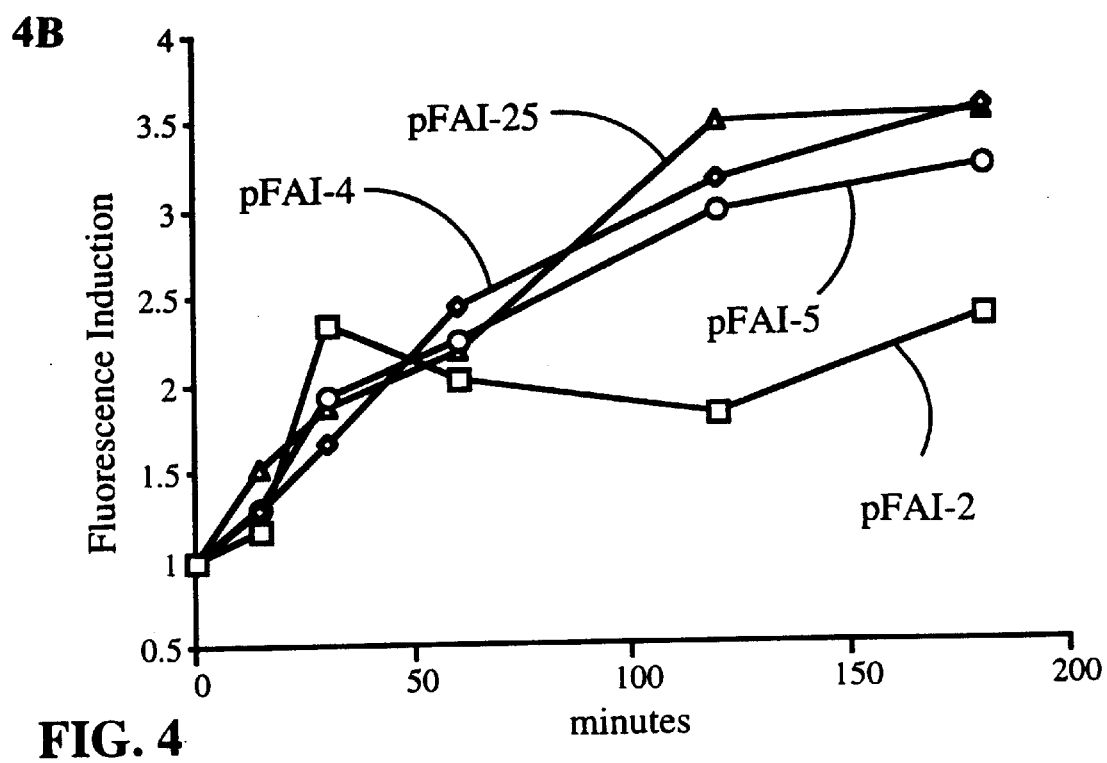
FIG. 4

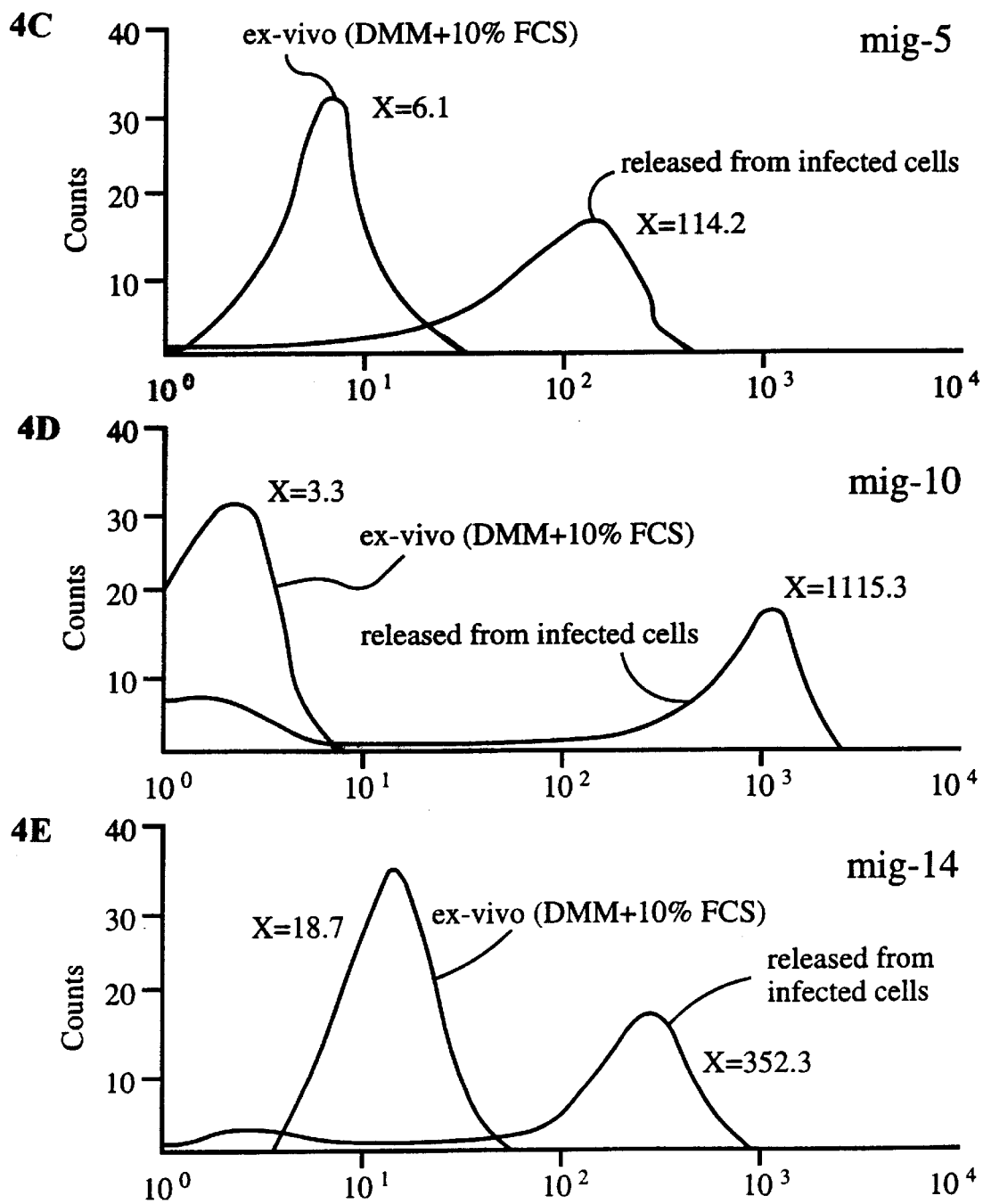

FLOURESCENCE-BASED ISOLATION OF DIFFERENTIALLY INDUCED GENES

RELATED APPLICATION DATA

This application is a continuation-in-part of U.S. patent application Ser. No. 08/791,332, filed Jan. 31, 1997 now issued as U.S. Pat. No. 5,804,387, which is based on U.S. Provisional Patent Application No. 60/010,960, filed Feb. 1, 1996. The above-cited applications are herein incorporated by reference.

U.S. GOVERNMENT RIGHTS

This invention was made with U.S. Government support under grant No. AI 36396 awarded by the National Institutes of Health. The U.S. Government has certain rights in the invention.

FIELD OF THE INVENTION

This invention relates generally to the field of microbiology. More particularly, it relates to differential fluorescence-based isolation of regulatory elements which are activated in response to specific environmental stimuli.

BACKGROUND OF THE INVENTION

Many intracellular pathogens survive in host organisms by coordinately regulating the expression of a wide spectrum of genes in response to their surroundings. This adaptation includes not only metabolic and physiological adjustments to new nutritional requirements, but also the synthesis of proteins necessary to circumvent the host organism's anti-microbial arsenal. For example, bacteria survive in phagocytes by expressing certain genes in response to the phagocytic environment. Since a microbe's ability to survive in the host correlates with its ability to cause disease, the identification of genes that are preferentially transcribed in the in vivo environment of the host is central to our understanding of how pathogenic organisms mount a successful infection. For further information on the relationship between gene expression and pathogen survival in hosts, see the articles by Mekalanos in *J. Bacteriol.* 174:1 (1992), Mahan et al. in *Escherichia coli and Salmonella typhimurium* F. C. Neidhart, Ed. (ASM Press, Washington D.C., 1996), vol. II, pp. 2803, Fields et al. in *PNAS USA* 83:5189 (1986), and Horwitz in *J. Exp. Med.* 166:1310 (1987).

Recently, the isolation of preferentially-induced genes has been made possible with the use of sophisticated promoter traps (e.g. IVET) that are based on conditional auxotrophy complementation or drug resistance. In one IVET approach, various bacterial genome fragments are placed in front of a necessary metabolic gene coupled to a reporter gene. The DNA constructs are inserted into a bacterial strain otherwise lacking the metabolic gene, and the resulting bacteria are used to infect the host organism. Only bacteria expressing the metabolic gene survive in the host organism; consequently, inactive constructs can be eliminated by harvesting only bacteria that survive for some minimum period in the host. At the same time, constitutively active constructs can be eliminated by screening only bacteria which do not express the reporter gene under laboratory conditions. The bacteria selected by such a method contain constructs that are selectively induced only during infection of the host. The genome fragments in such constructs make promising therapeutic targets. For information on IVET see the articles by Mahan et al. in *Science* 259:686–688 (1993), Mahan et al. in *PNAS USA* 92:669–673 (1995), Heithoff et al. in *PNAS USA* 94:934–939 (1997), and Wang et al. in *PNAS USA*. 93:10434 (1996).

IVET has been limited to bacterial pathogens with tractable genetic systems because of its requirement for high frequencies of homologous recombination and extensive strain manipulation prior to gene selection. In IVET, the library of constructs is made by recombination into the chromosome; consequently, building a representative library can be difficult and labor-intensive. The technique's reliance on conditional auxotrophic complementation or drug resistance limits its use to organisms with particular nutritional requirements or antibiotic sensitivity. Gene fusions that are transcriptionally silent under laboratory conditions must be manually screened, a step which is not only biased but also time-consuming. The use of lacZ or other conventional reporter genes requires the addition of substrates to the bacteria. In addition, the method is limited to the measurement of gene activity on a populational basis, and is sensitive to the bacterial load present within cells and to the effect of microenvironments on enzymatic activity (e.g., lacZ is irreversibly denatured below pH 5.5).

OBJECTS AND ADVANTAGES OF THE INVENTION

Accordingly, it is a primary object of the present invention to provide a method of rapidly and efficiently isolating regulatory elements which are selectively active in the presence of a stimulus. It is another object to allow isolation of selectively active regulatory elements from a library comprising a mixture of cells containing different regulatory elements. Another object of the invention is to allow identification and isolation of selectively active regulatory elements independently of nutritional requirements and drug susceptibility. Another object is to provide a selection method that is semi-automated, and avoids biases inherent to manual screening. Another object is to provide a selection method that is not biased by absolute levels of selectable marker expression. Yet another object is to allow a selection method suitable for analyzing the effects of transient stimuli on regulatory element activity. Another object of the invention is to provide a multiparametric (e.g. multicolor) analysis method allowing the isolation of a regulatory element that is selectively active in the presence of a particular stimulus that has a desired effect on another regulatory element. A further object of this invention is to identify genes regulated by selectively active regulatory elements. Another object of this invention is to enable sorting bacterial cells by FACS according to differential levels of expression of a coding sequence encoding a fluorescent marker.

SUMMARY OF THE INVENTION

The present invention provides a method for identifying and isolating regulatory elements that are selectively active in the presence of an environmental stimulus. The method begins with establishing a nucleic acid library comprising nucleic acids of interest operatively connected to coding sequences encoding a fluorescent marker. At least some of the nucleic acids of interest are regulatory elements such as promoters, enhancers or silencers, operatively connected to the coding sequences. The nucleic acid library comprises a mixture of vectors, and is transfected into a target cell population. Cells of the target cell population are sorted by fluorescence activated cell sorting (FACS), according to fluorescence signals indicative of intracellular levels of the fluorescent marker in the presence and the absence of an extracellular stimulus. Regulatory elements which are selectively active in the presence of the stimulus are then isolated from the library according to the measured fluorescence signals.

DESCRIPTION OF THE FIGURES

FIG. 2 shows fluorescence intensities of wild-type GFP and a mutant of the present invention, excited at 488 nm, with and without inducer.

FIG. 3-A illustrates a differential fluorescence induction enrichment strategy for isolating regulatory elements selectively induced at low pH, according to the present invention.

FIG. 3-B shows a preferred differential fluorescence induction enrichment strategy for isolating regulatory elements selectively induced in target cells during infection of host cells, according to the present invention.

FIGS. 4-A and 4-B shows induction kinetics for a number of acid-inducible promoters isolated according to a method of the present invention.

FIGS. 4-C, 4-D and 4-E shows FACS data for three macrophage-inducible promoters isolated according to a method of the present invention, for bacteria grown in isolation from macrophages and bacteria released from infected macrophages.

DETAILED DESCRIPTION

Libraries

Figure 1:
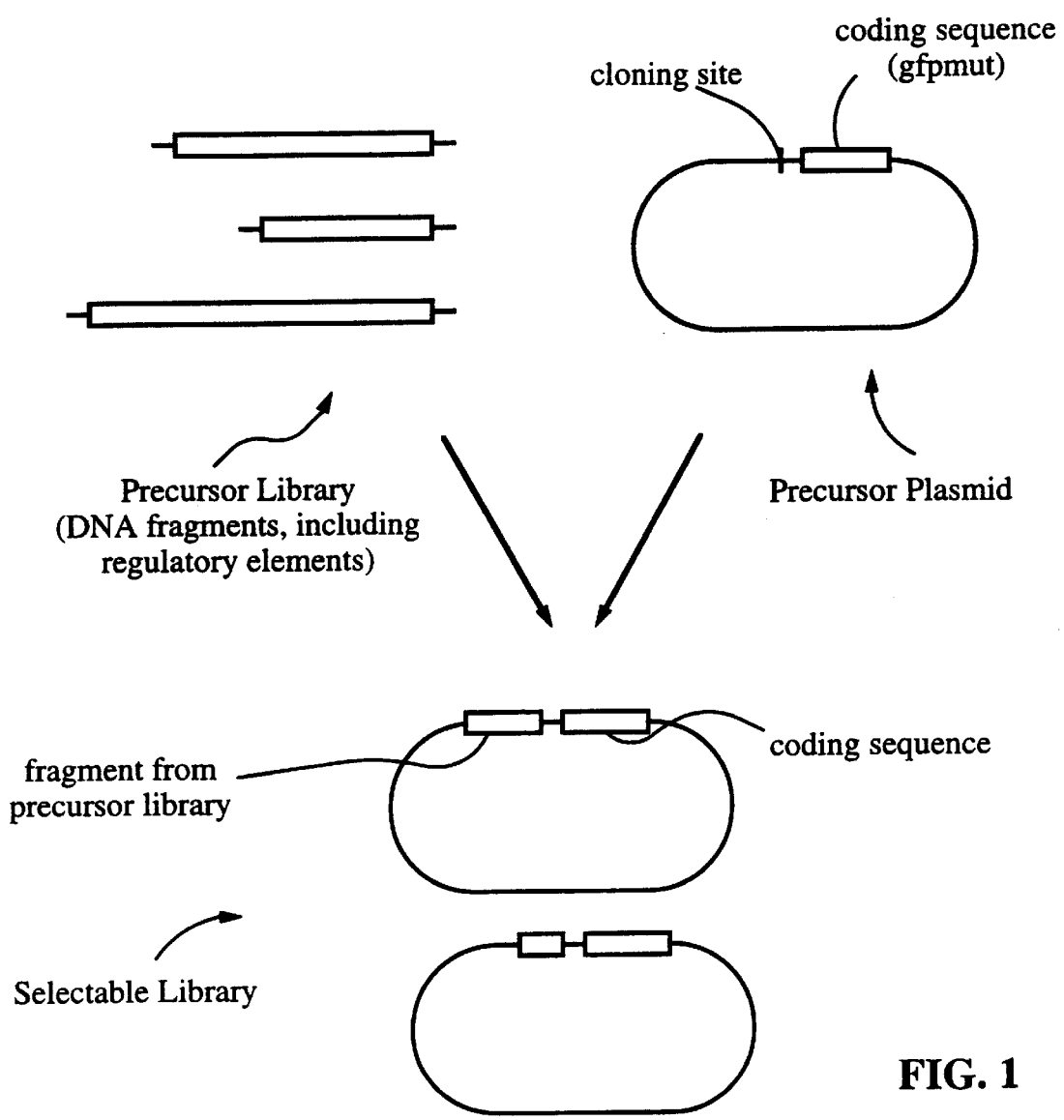
FIG. 1 illustrates schematically a process of building a selectable plasmid library according to the present invention.

Techniques for generating libraries of nucleic acids of interest are well known in the art. For information on such techniques see for example J. Sambrook et al., eds., *Molecular Cloning: A Laboratory Manual*, 2nd edition, Cold Spring Harbor Laboratory Press, 1989, which is herein incorporated by reference.

FIG. 1 illustrates schematically a process of building a selectable library, according to a preferred embodiment of the present invention. The selectable library is generated by cloning fragments of a precursor nucleic acid library into a cloning site situated in a predetermined position relative to a coding sequence. The expression levels of the coding sequence determine the intracellular levels of a fluorescent marker in cells expressing the coding sequence. Preferably, the coding sequence encodes a fluorescent protein marker such as the green fluorescent protein (GFP). Alternatively, the coding sequence may encode a protein whose production indirectly leads to the formation of a fluorescent marker; such a protein may be an enzyme (e.g. β-galactosidase or luciferase) capable of modifying (e.g. cleaving or oxidizing) a non-fluorescent precursor of the fluorescent marker, to generate the fluorescent marker.

The cloning site is situated relative to the coding sequence such that DNA fragments inserted in the cloning site are operatively connected to the coding sequence: if the fragments are suitable regulatory elements, they regulate the expression of the coding sequence. For the isolation of promoters, the cloning site is preferably in front of a coding sequence lacking a promoter, such that promoters inserted in the cloning site direct the expression of the coding sequence. Various positions of the cloning site relative to the coding sequence may be suitable for the isolation of other regulatory elements, as will be apparent to the skilled artisan.

Preferably, the cloning site is provided within a precursor plasmid containing the coding sequence, as illustrated in FIG. 1. The plasmid is capable of replication within target cells in which the plasmid is to be inserted. Alternatively, the cloning site may be provided within a target cell chromosome; some organisms, such as lower eukaryotes, are particularly suited for building functional fusion libraries by integration into the chromosome.

The precursor library comprises various nucleic acids of interest. The precursor library includes some regulatory elements (e.g. promoters, enhancers, silencers, transcription terminators), but need not consist solely of regulatory elements. Preferably, the precursor library consists of a collection/mixture of fragments representative of the entire genome of the target organism, generated by digesting a sufficient quantity of DNA of the organism with a suitable restriction enzyme. In particular, the chance that a particular sequence of the target cell genome is represented in the precursor nucleic acid library is preferably higher than 90%, and ideally higher than 99%. The degree to which the precursor nucleic acid library represents the target cell genome can be varied according to the application. Generating libraries representative of a given genome is well known in the art.

The selectable library is inserted into a target cell population, preferably of the same strain as the fragments of the precursor library. The target cells may be pathogens such as bacteria, fungi, viruses, or protozoa. In a preferred embodiment of the present invention, the target cells are potentially pathogenic gram negative bacteria, e.g. *Salmonella typhimurium*, *E. Coli*, *Haemophilus influenzae*, *Pseudomonas Aeruginosa*, or of the genera Moraxella or Legionella. In other embodiments, they are pathogenic gram positive bacteria, e.g. *Helicobacter pylori* or *Mycobacterium tuberculosis*, or of the genera Staphylococcus, Streptococcus or Enterococcus. Other suitable target cells include Mycoplasma and pathogenic fungi such as Candida or Aspergillus.

The target cell population preferably consists of a mixture of cells containing different library elements, rather than a collection of individually-isolated cultures each containing a single library element. Individual cells of the mixture can be analyzed by fluorescence activated cell sorting, as explained below.

Fluorescent Markers

Fluorescent markers used in a method of the present invention are preferably as bright as possible per unit of fluorescent marker produced. Brighter markers allow the isolation of regulatory elements which are modulated to a relatively limited extent by a stimulus of interest. Brighter markers are especially desirable for analysis of heterogeneous cell populations, in which intrapopulation fluorescence variability may obscure the stimulus-dependence of the fluorescence of any given cell.

Many fluorescent markers, including various variants of GFP, may be suitable for use in a selection method of the present invention. For information on prior-art GFP variants see U.S. Pat. Nos. 5,491,084 and 5,625,048, herein incorporated by reference. Other potentially suitable fluorescent markers include phycobiliproteins such as phycoerythrin, as well as luciferase-dependent markers.

The present invention is facilitated by the discovery of the relatively bright FACS-optimized green fluorescent protein (GFP) mutant classes described in the above-referenced co-pending patent application and in the article by Cormack et al. in *Gene* 173, 33 (1996), herein incorporated by reference. A set of mutation positions of the mutant GFP comprises at least one of position 64, 68 or 72. The set of positions further comprises a second position, preferably position 65. The set of positions consists of all amino acid positions in the mutant GFP at which an amino acid differs from the corresponding amino acid of wild-type GFP.

A set of mutations of the mutant protein comprises a first mutation selected from F64L, V68L and S72A. Preferably the set of mutations further comprises a second mutation selected from S65T, S65A and S65G. The set of mutations consists of all mutations in the mutant protein, relative to wild-type GFP. In one embodiment, the set of mutations consists essentially of F64L and S65T. In another embodiment, the set of mutations consists essentially of V68L, S72A and S65A. In still another embodiment, the set of mutations consists of S72A and S65G.

The set of mutations preferably comprises at least two mutations within a target mutagenesis region containing the chromophore. The target mutagenesis region consists substantially of a sequence of less than 20 amino acids. In one embodiment, the set of mutations consists essentially of two mutations.

In particular embodiments, the set of mutations comprises a subset selected from (F64L, S65T), (S65A, V68L, S72A) and (S65G, S72A). Preferably, the set of mutations consists essentially of one of the subsets. In three different embodiments of the present invention, amino acid sequences containing the GFP chromophore comprise Leu Thr Tyr Gly Val Gln Cys Phe Ser (SEQ ID NO:1), Phe Ala Ala Tyr Gly Leu Gln Cys Phe Ala (SEQ ID NO:2) or Phe Gly Tyr Gly Val Gln Cys Phe Ala (SEQ ID NO:3), respectively. A 488-nm-excited fluorescence signal from the mutant protein is higher than a 488-nm-excited fluorescence signal from wtGFP expressed under similar conditions (similar promoter, cell, temperature, etc.). Mutants GFP of the present invention are significantly brighter than wtGFP particularly at high temperatures (e.g. 37° C.), in part because of the better folding properties of the mutants at high temperatures. In particular, the solubility of mutants of the present invention is significantly higher than the solubility of wtGFP in cells grown at 37° C.

The present invention provides mutants with single excitation peaks substantially at 490 nm or 500 nm, and emission peaks substantially at 510 nm. The mutants excitation spectra are optimized for excitation using the 488 nm line of Ar ion lasers used in typical FACS equipment. The three mutant classes include mutants having a (F64L, S65T) mutation subset, a (S65A, V68L, S72A) mutation subset, or a (S65G, S72A) mutation subset, relative to wild-type GFP. The mutants allow the isolation of selectively active regulatory elements which are less than twenty times (in particular less than five times) more active in the presence of a stimulus than in the absence of the stimulus, for example from a heterogeneous cell population comprising a library representative of the *Salmonella typhimurium* genome (see examples below).

The above-described GFP mutants exhibit a number of physical characteristics that provide distinct advantages over wild-type GFP when the proteins are used as biological markers or reporter proteins. Wild-type GFP has an excitation maximum at 395 nm and an emission maximum at 510 nm. The GFP mutants have excitation maxima between 488 nm and 500 nm, with emission maxima around 510 nm. The mutants fluoresce at substantially higher intensity levels (per unit protein) than wild-type GFP, upon excitation with 488 nm light. In *E. coli*, maximal fluorescence of the mutant GFPs was measured to be 75–100 fold higher than that reached with wild-type GFP. In addition, while wild-type GFP has a propensity to precipitate into non-fluorescent inclusion bodies, the mutants are highly soluble. The high solubility of the mutant proteins contributes to the increased fluorescence of the bacteria expressing the mutant GFP proteins. The advantages of the mutant GFPs are especially evident at high temperatures, where the mutants exhibit improved folding properties.

Relative to wtGFP, the mutants exhibit reduced chromophore. formation times. Wild-type GFP requires up to 2 hours before half-maximal fluorescence can be seen, while mutant fluorescence is observable within minutes of induction. Finally, fluorescence of these mutant GFPs does not depend on the bacterial strain in which they are expressed. Fluorescence intensity. increases were seen when the mutant GFPs were expressed in *E. coli* strains XA90 and DH12S, in *Yersinia pseudotuberculosis, Salmonella typhimurium*, Mycobacteria spp., and *Helicobacter pylori*.

The brightness of the above-described mutants further allows differential sorting of bacteria by flow cytometry, according to GFP levels. Bacteria can be sorted from a bacterial pool according to differential (high, medium, low) levels of expression of a coding sequence encoding a mutant. Differential sorting is possible due to the increased brightness of the above-described GFP mutants, which allows for differential distinctions between fluorescence levels. FIG. 2 shows histograms of numbers of cells as a function of fluorescence intensity for a wild-type GFP strain (top histograms) and an enhanced-GFP strain (bottom histograms) under the control of a tightly regulated isopropyl-$\beta$-D-thiogalactopyranoside (IPTG) inducible promoter, excited at 488 nm, with and without induction with IPTG. The integral mean fluorescent intensities were X=2.835 for the wt GFP strain in the presence of IPTG (inducer), and X=186.1 for the mutant strain in the presence of IPTG. As FIG. 2 illustrates, wtGFP provides a relatively limited dynamic range of fluorescence values, and does not allow adequately distinguishing between differential expression levels, while the enhanced-GFP strain provides a large dynamic range of fluorescence values (larger than 10, and in particular larger than 50), which allows adequately distinguishing between differential levels of expression.

GFP has been used previously for various applications. For information on prior described or suggested uses of GFP see for example the above-incorporated U.S. Pat. Nos. 5,491,084, and 5,625,048, as well as U.S. Pat. No. 5,569,588.

Stimuli

The target cell population may be subjected to a variety of stimuli capable of activating some regulatory elements in the target cells. Suitable stimuli include the presence, or relative or absolute absence, of compounds of interest such as drugs, drug candidates, hormones, heavy metals, organic solvents, and species-specific factors. Other suitable stimuli include environmental factors such as extracellular pH or temperature. In one embodiment, bacteria capable of surviving in the acidic phagosomes of host macrophages are subjected to an acidic environment, for isolating bacterial regulatory elements activated by low intracellular pH.

The stimuli need not be simple; the present invention is well suited for analyzing complex stimuli such as those encountered by pathogens during infection. Preferably, the target cells are exposed to the internal environment of a host, during infection of the host by the target cells. In a preferred embodiment, the target cells are exposed to the intracellular environment of host cells (e.g. mammalian cells) under infection, and are analyzed within the host cells. Alternatively, the target cells are exposed to an extracellular environment (e.g. serum) of the host during infection of the host.

The stimulus of interest is applied for a time period sufficient to allow detectable expression of the fluorescent marker. The fast chromophore formation times of the preferred mutant GFPs described above allow the analysis of transient stimuli, such as stimuli acting for periods on the order of minutes (less than one hour).

Analysis and Isolation

FIG. 3-A illustrates a differential fluorescence induction enrichment strategy suited for isolating promoters selectively induced at low pH (stimulus), according to the present invention.

An initial target cell population (e.g. bacterial or fungal cells) contains a selectable library of DNA fragments including promoters. Fluorescence signals indicative of intracellular levels of the fluorescent marker are used to sort cells of the target cell population by fluorescence activated cell sorting (FACS). The use of FACS allows for the semi-automation of this selection methodology and avoids biases inherent to manual screening. In particular, the use of FACS allows rapidly analyzing the entire target cell population, by sorting a cell mixture containing the entire selectable library in a single step.

The target cells are exposed to a low pH (e.g. pH 4.5) such that marker levels within the target cells reflect the activity of the corresponding DNA fragments (equivalently, the expression of the coding sequence) at the low pH. The target cell population is sorted at the low pH (Step 1) into a fluorescent subpopulation and a non-fluorescent subpopulation. The threshold(s) separating the fluorescent and non-fluorescent subpopulation is/are chosen according to the application, for example to control enrichment efficiencies or selectivities.

The non-fluorescent subpopulation contains a sublibrary of inactive DNA fragments and is eliminated. The fluorescent subpopulation is grown at neutral pH (no stimulus) until the intracellular marker levels reflect the expression of the coding sequence at pH 7.0, to generate an amplified fluorescent target cell subpopulation. The amplified subpopulation is then sorted into a constitutively fluorescent subpopulation and a selectively fluorescent subpopulation (Step 2).

Preferably, the fluorescence threshold for separating the constitutively fluorescent and selectively fluorescent subpopulations is the same as the threshold used for separating the fluorescent and non-fluorescent subpopulations. More generally, the fluorescence threshold(s) are chosen to ensure the isolation of differentially-induced regulatory elements. Various thresholds may be chosen and/or evaluated, according to desired per-step enrichment efficiencies and method sensitivities.

The constitutively fluorescent population, which is fluorescent in the absence of the stimulus, contains constitutively active regulatory elements and is eliminated. The selectively fluorescent population, which is non-fluorescent in the absence of the stimulus, contains selectively active regulatory elements and is retained. The selectively fluorescent population is amplified and the above-described sorting steps are repeated if desired (Step 3, etc.). The cells obtained following the sequential sorting contain regulatory elements that are selectively active (activated) only in the presence of the stimulus.

Preferably, the order of the sorting steps performed is that shown in FIG. 3-A. In a library in which most elements are inactive, the sorting order of FIG. 3-A eliminates most of the library elements in the first sorting step, thus simplifying subsequent processing steps. In some applications, however, it may be suitable to first sort out cells expressing the marker constitutively, in the absence of the stimulus of interest. Inactive fragments are then separated from selectively active regulatory elements in a second selection step performed in the presence of the stimulus.

FIG. 3-B illustrates the sorting steps preferably performed for selecting promoters which are selectively active in pathogens during infection of host cells. An initial host cell population is generated by infecting host cells with an initial target cell (pathogen) population. The target cell population is sorted within the host cells into fluorescent and non-fluorescent subpopulations (Step 1); that is, the host cells are sorted according to levels of the fluorescent marker within corresponding target cells. The host cells are lysed, and the resulting target cells are grown in isolation from the host (Step 2), for a sufficient period of time to allow the marker levels within the target cells to reflect the expression of the coding sequence in the absence of the host. The target cells are then sorted directly, i.e. not within host cells (Step 3), to isolate selectively fluorescent target cells. The enrichment process may be repeated sequentially by infecting host cells with the isolated selectively fluorescent target cells (Step 4, etc.)

More generally, a host may be infected with the target cell population, and the target cells sorted directly (outside host cells) according to fluorescent marker levels within the host. For example, the target cells may be subjected to serum from the host during infection, and sorted according to fluorescent marker levels reflecting the complex species-specific stimulus presented by the serum.

In a multiparametric analysis embodiment, the cells of the target cell population comprise a first fragment of the selectable library connected to a first marker, as well as a known regulatory element connected to a coding sequence encoding a second fluorescent marker. The second fluorescent marker is spectrally distinguishable from the first marker, such that the two markers can be analyzed while simultaneously present within the same cell. Selectively active regulatory elements are isolated from the selectable library according to intracellular levels of the two markers in the presence and absence of the stimulus of interest. Such a multiparametric analysis method allows focusing on stimuli that have a desired effect on the known regulatory element, for example stimuli which induce expression of a known gene.

Post-Isolation Analysis

The complexity of all libraries (initial, intermediate, final) may be analyzed by polymerase chain reaction (PCR) using primers flanking the cloning site, after extracting the fragments of interest (e.g. plasmid DNA) from the target cells. Nucleic acids amplified by PCR are run on a gel using electrophoresis. The number of bands in the gel is indicative of the number of different fragments in the library of interest. The amplified nucleic acids may also be sequenced by well-known methods.

It is possible to determine the orientation of the library fragments within extracted plasmids. This step is useful for separating selectively active regulatory elements from other non-regulatory elements which happen to activate transcription. The nucleic acids inserted in the plasmids are sequenced, and the sequences are matched against the known genome sequence of the organism. Regulatory element sequences will generally be oriented in the same direction with respect to the regulated gene as with respect to the coding sequence, while non-regulatory element sequences that happen to activate transcription may read in the opposite direction.

Several other tests may be used to confirm that the measured activation of regulatory elements is not due to experimental artifacts. Levels of fluorescent marker mRNA may be measured in the presence and absence of the stimulus; increased mRNA levels in the presence of the stimulus suggest that fluorescence differences are not due to altered marker stability or chromophore formation. If most regulatory elements in the library do not appear to be active in the presence of the stimulus, it is unlikely that fluorescence increases in the presence of the stimulus are due to the action of the stimulus on the marker, rather than on the regulatory element. If a particular regulatory element appears to be selectively active both in a plasmid and in the target cell genome, it is likely that the increased activity in the presence of the stimulus is not due to an effect of the stimulus on plasmid copy number.

Applications

A particularly useful application of the present invention includes identifying targets for drug screening or vaccine development. First, a selectively active regulatory element is isolated as described above and sequenced. The gene regulated by the regulatory element in its organism of origin is identified by art-known methods. Identification of the gene corresponding to a selectively active regulatory element allows measuring the effect of a compound of interest on the expression of the gene in the organism of origin, measuring the effect of a compound of interest on the biological activity of the gene product, or measuring the effect of the gene product on the immune response of a patient. As will be clear to the skilled artisan, there are many other potential applications of an isolation method of the present invention.

The following examples indicate specific ways in which to carry out the present invention, in particular for isolating regulatory elements selectively induced under acid shock and during infection of a host. These examples should not be construed to limit the invention.

EXAMPLE 1

Isolation of Acid-Inducible Promoters

The scheme illustrated in FIG. 3-A was used to isolate *S. typhimurium* promoters that are selectively active in acidic conditions, such as the conditions encountered in macrophage phagosomes. For information on isolation of *S. typhimurium* promoters selectively active during acid shock, see the article by Valdivia et al. in *Molecular Microbiology* 22(2):367–378 (1996) which is herein incorporated by reference.

A set of promoter libraries were made by inserting random *S. typhimurium* DNA fragments (0.4–1.6 kb) into the plasmid pFPV25, creating gene fusions to a promoterless gfpmut, and transformed into *S. typhimurium*. *S. typhimurium* strain SL1344 (rpsL hisG xyl) was used for all DNA manipulations and transformations. The promoter-trap plasmid, pFPV25, was constructed by inserting an EcoRI-HindIII fragment containing a promoterless gfpmut3 (described in the above-referenced co-pending patent application and in the article by Cormack et al. in *Gene* 173:33–38 (1996)) into plasmid pED350 (colE1, b1a, mob) (Derbyshire et al., *Mol. Gen. Genet.* 206:161–168 (1987)). Total DNA from SL1344 was partially digested with Sau3A, size fractionated (0.4–1.6 kb) from an agarose gel and ligated into the BamHI site of pFPV25. Five libraries of SL1344 DNA fragments in pFPV25 were constructed and electroporated into SL1344. Each library consisted of approximately two thousand independent DNA inserts.

During the analysis of the promoter fusion library, several constitutive promoters were partially characterized. One of these promoter fusions (pFPV25.1) was used as a control in further analysis steps, since it was found not to be regulated in response to acid shock or the macrophage environment. Sequence information indicates that pFPV25.1 contains the promoter region of *S. typhimurium* rpsM which encodes for the ribosomal protein S13.

Bacterial cell suspensions were analyzed in a FACScan and sorted in a FACStar$^{Plus}$ (Becton Dickinson) machine equipped with argon lasers emitting at 488 nm. Bacteria were detected by side scatter, as previously described in the article by Valdivia et al. in *Gene* 173: 47–52 (1996). Fluorescein and side scatter data were collected with logarithmic amplifiers.

The initial selectable library and subsequently sorted sublibraries were grown to midlog phase at 30° C. For selections during acid shock, a 50 ml subculture from the midlog-grown library was used to inoculate 3 mL of Luria broth equilibrated to pH 4.5 with HC1. After a 90 min induction, the culture was analyzed by FACS and the bacterial population exhibiting fluorescence intensity greater than an identically treated SL1344 culture was sorted. The collection threshold in this sort was set so that greater than 99% of non-productive (non-fluorescent at pH 4.5) gfpmut fusions were excluded.

This population was amplified overnight on L-agar plates (100 μg/ml amp). This first passage library was collected and used to inoculate 5 mL-broth, grown to midlog and a 50 μL aliquot was used to inoculate 3 mL of fresh L-broth at pH 7.0 for 90 min. Non-fluorescent bacteria, represented by the bottom 10% of the total fluorescent population, were sorted and amplified as above. This non-fluorescent population was grown in L-broth at pH 4.5 (90 min) one final time and the most fluorescent bacteria (top 10% of the total population) were collected.

EXAMPLE 2

Characterization of Isolated Acid-Inducible Promoters

Eight fluorescent acid-inducible promoters (FAI) isolated following the final sorting step were characterized in detail. The promoters were sequenced and compared with available DNA sequence databases. Fluorescence was measured for each promoter following induction by acid shock or infection of macrophage-like cells (RAW 264.7). Table 1 lists several characteristics of the characterized promoters.

TABLE 1

| Promoter Construct | Insert Size (bp) | Homology | fold-induction in vitro at pH 4.5 | fold-induction in RAW 264.7 |
| --- | --- | --- | --- | --- |
| FAI-1 | 430 | aas | 17.1 ± 2.6 | 18.2 ± 7.3 |
| FAI-2 | 868 | dps | 2.6 ± 0.4 | 5.1 ± 1.4 |
| FAI-3 | 511 | marR | 5.3 ± 3.3 | not distinguishable |
| FAI-4 | 783 | pagA | 3.9 ± 0.3 | 12.4 ± 2.2 |
| FAI-5 | 773 | rna | 3.5 ± 0.4 | 2.9 ± 0.3 |
| FAI-15 | 663 | pbpA | 5.0 ± 0.6 | not distinguishable |
| FAI-23 | 1436 | pbpA | 5.0 ± 0.6 | not distinguishable |
| FAI-25 | 898 | emrR | 3.7 ± 0.2 | 1.0 ± 0.1 |

To obtain the acid-shock data, aliquots (0.1 mL) from midlog phase cultures from individual clones were used to inoculate 3 mL of L-broth at pH 4.5 for five different time intervals (0, 15, 30, 60, 150 and 240 min). The data in Table 1 corresponds to the 240 minute time point. Fluorescence from 30,000 bacteria were read at each time point with a FACScan (Becton Dickinson). Quantitative measurements and distribution of fluorescence from the different acid-inducible gfpmut3 fusions was determined with the CellQuest software program (Becton Dickinson).

To obtain the macrophage-infection data, tissue culture wells for each FAI fusion were seeded with 5×10$^5$ RAW 264.7 macrophages in 1 mL of Dubelco's modified Eagle's medium (DMEM) supplemented with 10% fetal calf serum (FCS) and 1 mM glutamine. Approximately $10^6$ bacteria from a standing overnight culture in L-broth (supplemented with 100 μg/mL amp and 0.3M NaCl) were added to each well and spun onto the macrophage layer (×2000 g 5 min). After a 30 min infection, the monolayers were washed twice with fresh DMEM supplemented with 100 μg/mL amp, and the incubation was allowed to proceed for 3–4 h. Monolayers were then washed four times with phosphate-buffered-saline (PBS), placed on ice, lysed with 0.1 mL 1% Triton-X in PBS for 5 min, and diluted with 0.9 mL cold DMEM. Detergent-released bacteria were differentiated from the bulk of lysed macrophage particles by their forward and side scatter profiles. Thorough washing of the infected monolayers prior to detergent treatment is necessary to remove most extracellular organisms. Indeed, if the monolayers are not washed with PBS, a second distinct peak of bacterial-size particles with the same fluorescence intensity as bacteria exposed to tissue culture media alone is seen after Triton-X treatment. The size of this peak diminishes with each wash and thus represents extracellular bacteria (not shown). Samples were kept on ice until FACS analysis.

To determine levels of induction in response to macrophages, the level of fluorescence from detergent-released bacteria was compared to fluorescence from FAI promoter fusions that were exposed to tissue culture media (DMEM+10% FCS) alone. The kinetics of gfpmut expression by intracellular bacteria was determined by infecting macrophages for 0.5, 1, 2, 4 and 5 h. Levels of bacterial fluorescence which could not be distinguished from background macrophage-debris fluorescence are marked "not distinguishable" in Table 1.

Induction values in Table 1 are relative to fluorescence data in the absence of stimulus (bacterial cells at 7.0 pH, not involved in macrophage infection). Maximal induction levels are shown as fold-increase in fluorescence intensity between inducing and non-inducing conditions, to minimize variability in relative fluorescence measurements among independent experiments. The mean fold-induction and standard deviations were calculated from a minimum of three independent measurements. The relative mean fluorescence intensity of the constitutive control promoter fusion pFPV 25.1 (rpsM::gfpmut) was 275.3 at pH 4.5 and 280.2 at pH 7 (1.0-fold induction).

Recombinant DNA manipulations, PCR-amplification, and nucleotide sequencing followed previously described protocols (Sambrook et al., *Molecular Cloning: A Laboratory Manual*). DNA homologies with sequences in the available databases were determined with the program BLAST (National Center for Biotechnology Information at the National Library of Medicine), described in the article by Altschul et al. in. *J. Mol. Biol.* 215:403–410 (1990). Nucleotide sequences described above have been deposited in GenBank (Accession Numbers: U62708-U62714).

FIG. 4-A illustrates induction kinetics for plasmid constructs comprising the promoters listed in Table 1. SL1344 bearing each pFAI construct were subjected to pH 4.5 for different time intervals. The relative mean fluorescence intensity of 30,000 events was determined by FACS analysis for each time point. For ease of comparison among independent constructs, fluorescence induction has been normalized to fluorescence values at t=0. Maximal fluorescence values are as follows: pFAI-1 (229.36), pFAI-2 (2.38), pFAI-3 (8.96), pFAI-4 (3.57), pFAI-5 (3.23) pFAI-15/23 (5.49), and pFAI-25 (3.49). These measurements represent the relative mean fluorescence intensity of the bacterial populations as detected by the cytometer's sensors, and are representative of induction experiments performed on three independent days. As can be seen from FIG. 4-A, fluorescence was observable for all promoters within one hour of induction.

EXAMPLE 3

Isolation of Promoters Selectively Active in Macrophage Infection

The scheme illustrated in FIG. 3-B was used to isolate *S. typhimurium* promoters that are selectively active in *S. typhimurium* cells involved in macrophage infection.

Eight pools of plasmids containing DNA inserts (3–5K independent inserts/pool) were built as described above. The pools were used to transform SL1344, and were maintained separately during subsequent selections. Each pool was used to infect a monolayer of RAW 264.7 macrophage-like cells at a multiplicity of infection (MOI) of 5:1. After a six hour infection, the RAW 64.7 cells were gently scraped from the tissue culture wells, resuspended in cold Dubelco's modified Eagle media (DMEM) supplemented with 10% fetal calf serum (FCS) and analyzed in a FACStar$^{Plus}$ cytometer. Cells infected with a fluorescent bacterium were readily distinguished from uninfected cells or cells infected with *S. typhimurium* bearing unproductive gfp gene fusions.

Fluorescent RAW 64.7 cells were sorted, and *S. typhimurium* present within the fluorescent cells were recovered by treating the infected macrophages with 1% Triton-X. The released bacteria were grown for six hours in tissue culture media supplemented with 10% fetal calf serum (FCS) under the same environmental conditions as those used for the RAW 64.7 cells (37° C., 5% $CO_2$). FACS analysis of the recovered fluorescent bacterial population yielded bacteria with a wide range of fluorescence intensities. Bacteria with the lowest fluorescence (Lower 15%) in the absence of host cells were sorted as described above.

The low-fluorescing bacteria were collected, amplified on L agar plates, and used to reinfect RAW 64.7 cells at a MOI of 0.5 to 1. After six hours, infected cells that became fluorescent were sorted. Flow cytometric analysis of the macrophages showed a marked increase in the number of fluorescent infected cells as compared to infection with the initial library. The fluorescent cells were collected and the bacteria within recovered after RAW 64.7 cell lysis. Testing of independent clones revealed a marked enrichment for bacteria bearing gfp gene fusions with intracellular-dependent activity.

EXAMPLE 4

Characterization of Isolated Macrophage-Inducible Promoters

Individual bacterial clones recovered from infected macrophages following the last sorting step described in Example 3 were analyzed separately to confirm intracellular-dependent induction of the gfp gene fusion. The analysis was performed by comparing the fluorescence intensity of individual bacteria grown in tissue culture media with the fluorescence intensity of bacteria released from infected cells. Intracellular-dependent induction of the isolated gfp gene fusions was further confirmed by fluorescence microscopy. Approximately a third to a half of all bacterial clones that were recovered after one enrichment cycle contained a gfp gene fusion with host cell-dependent activity. Fourteen promoters with intracellular-dependent activity were isolated as described in Example 3.

The genes downstream of these promoters (macrophage-inducible genes, or mig) were isolated by recombinational cloning. Each plasmid bearing a mig::gfp fusion was mobilized into the *S. typhimurium* strain SL4702R (polA rpsL). This strain does not support the replication of ColE1 plasmids and thus the pFPV plasmid integrates by homologous recombination. Total DNA for each integrant was isolated, and 10 μg of DNA was digested either with HindIII or SphI. The digested DNA was religated and used to transform *E. coli* strain DH12S. Plasmid DNA was isolated from $Amp^R$ colonies, digested with restriction enzymes, and compared to predicted *S. typhimurium* chromosomal DNA fragments from Southern blot hybridizations. The captured DNA downstream of each mig promoter was sequenced by subcloning restriction enzyme-digested DNA fragments into the sequencing vector pBK-CMV (Stratagene) and by primer walking.

Table 2 lists fluorescence, homology, and putative function data for the fourteen migs isolated as described in Example 3.

TABLE 2

| Construct | Homology | Fold-induction in macrophages | Protein features and/or putative function |
|---|---|---|---|
| mig-1 | aas Y | 16.4 | phospholipid recycling |
| mig-2 | pag A/ugd | 16.6 | capsule biosynthesis |
| mig-3 | — | 31.1 | phage derived genes |
| mig-4 | phoS | 9.4 | phosphate transport |
| mig-5 | — | 24.1 | virulence plasmid lipoprotein |
| mig-7 | yjbA(orf o 156) | 15.2 | inner membrane protein |
| mig-10 | ssaH | 442.9 | type III secretion |
| mig-13 | orf f198 | 8.0 | transmembrane protein |
| mig-14 | — | 22.4 | — |
| mig-20 | — | 12.6 | — |
| mig-23 | himA | 14.9 | transcriptional regulator |
| mig-26 | exc(traT) | 9.4 | plasmid exclusion protein |
| mig-29 | hs/V | 23.7 | stress response |
| mig-30 | — | 11.1 | — |

The isolated DNA fragments (0.2–1.2 kb) were sequenced and compared to the available DNA sequence databases at the National Center for Biotechnology Information (NCBI). Putative functions were assigned either when a particular gene had been previously described in *S. typhimurium* or when the function of a close homologue (>50% aa identity) had already been determined. For promoters regions with no significant homology to previously described genes or with homology to genes with unknown function, flanking DNA was isolated by recombinational cloning and fully sequenced. ORFs, deduced amino acid sequence and protein motifs were determined with programs from the Wisconsin GCG package. Five ORFs downstream of macrophage-inducible promoters were inactivated either by insertion of a kanamycin resistance gene flanked by transcriptional terminators (Wkn) or by insertion of the suicide vector pGP704 ($AMp^R$) into coding regions.

FIG. 4-B shows the results of FACS scans of bacteria grown in isolation, and bacteria involved in infection, for three of the promoters listed in Table 2. *S. typhimurium* bearing three independent mig::gfp fusions were used to infect RAW 64.7 cells for 6 h. Histograms show the relative fluorescence intensity of bacteria grown under ex-vivo conditions (DMEM+10% FCS) for 6 h, and fluorescence of bacteria released from infected cells after 1% Triton-X lysis (see Example 2). Analysis and quantitation of fluorescence was performed with CellQuest software (Becton Dickinson). The three histograms illustrate that the isolation of the mig::gfp fusions was based on differential, rather than absolute, levels of gfp expression.

All publications and patent applications cited above are herein incorporated by reference in their entirety for all purposes to the same extent as if each individual publication or patent application were specifically and individually indicated to be so incorporated by reference. Although the present invention has been described in some detail by way of illustration and example for purposes of clarity and understanding, it will be apparent that certain changes and modifications may be practiced within the scope of the appended claims.

What is claimed is:

1. A method of isolating a selectively active regulatory element, comprising the steps of:
   a) establishing a selectable library comprising regulatory elements operatively connected to a coding sequence encoding a mutant green fluorescent protein marker;
   b) inserting said selectable library into a target cell population; and
   c) isolating said selectively active regulatory element from said selectable library using fluorescence activated cell sorting to sort cells of said target cell population according to expressed levels of said green fluorescent protein marker, which are indicative of the effect of a presence or an absence of an extracellular stimulus affecting said selectively active regulatory element, wherein said fluorescent marker has a higher fluorescence intensity per unit expressed than a wild-type Aequorea victoria green fluorescent protein upon excitation with 488 nm light, wherein said mutant green fluorescent protein comprises a mutation at position 72.

2. The method of claim 1, wherein said mutant green fluorescent protein comprises a set of mutations selected from a group consisting of (F64L, S65T) (S65A, V68L, S72A), and (S65G, S72A).

3. The method of claim 1, wherein said selectively active regulatory element is less than twenty times more active in the presence of said stimulus than in t he absence of said stimulus.

4. The method of claim 1, further comprising a step of identifying a gene regulated by said selectively active regulatory element.

5. The method of claim 1, wherein said mutant green fluorescent protein further comprises a mutation at position 65.

6. The method of claim 1, wherein said mutant green fluorescent protein further comprises a mutation at position 68.

7. The method of claim 1, wherein said mutant green fluorescent protein further comprises a mutation at positions 65 and 68.

8. The method of claim 1, wherein said mutant green fluorescent protein comprises an S72A mutation.

9. The method of claim 8, wherein said mutant green fluorescent protein further comprises an S65A mutation.

10. The method of claim 8, wherein said mutant green fluorescent protein further comprises a V68L mutation.

11. The method of claim 1, wherein said mutant green fluorescent protein further comprises an S65A and a V68L mutation.

12. The method of claim 11, wherein said mutant green fluorescent protein further comprises an S65G mutation.

13. The method of claim 1, wherein said mutant green fluorescent protein comprises the amino acid sequence as set forth in SEQ ID NO:1.

14. The method of claim 1, wherein said mutant green fluorescent protein comprises the amino acid sequence as set forth in SEQ ID NO:2.

15. The method of claim 1, wherein said mutant green fluorescent protein comprises the amino acid sequence as set forth in SEQ ID NO:3.

* * * * *

UNITED STATES PATENT AND TRADEMARK OFFICE
CERTIFICATE OF CORRECTION

PATENT NO: 5,994,077
DATED: November 30, 1999
INVENTOR(S): Raphael H. Valdivia, Brendan P. Cormack and Stanley Falkow It is certified that error appears in the above-identified patent and that said Letters Patent is hereby corrected as shown below:

On the title page: Item [54] and Column 1, line 3,
Please correct in the title "FLOURESCENCE-BASED" to read as ---FLUORESCENCE-BASED---

Signed and Sealed this

Thirtieth Day of January, 2001

*Attest:*

Q. TODD DICKINSON

*Attesting Officer*  *Director of Patents and Trademarks*

SEQUENCE LISTING

<160> NUMBER OF SEQ ID NOS: 3

<210> SEQ ID NO 1
<211> LENGTH: 9
<212> TYPE: PRT
<213> ORGANISM: Artificial Sequence
<220> FEATURE:
<223> OTHER INFORMATION: synthetic mutation in green fluorescent protein

<400> SEQUENCE: 1

Leu Thr Tyr Gly Val Gln Cys Phe Ser
1               5

<210> SEQ ID NO 2
<211> LENGTH: 10
<212> TYPE: PRT
<213> ORGANISM: Artificial Sequence
<220> FEATURE:
<223> OTHER INFORMATION: synthetic mutation in green fluorescent protein

<400> SEQUENCE: 2

Phe Ala Ala Tyr Gly Leu Gln Cys Phe Ala
1               5                   10

```
<210> SEQ ID NO 3
<211> LENGTH: 9
<212> TYPE: PRT
<213> ORGANISM: Artificial Sequence
<220> FEATURE:
<223> OTHER INFORMATION: synthetic mutation in green fluorescent protein

<400> SEQUENCE: 3

Phe Gly Tyr Gly Val Gln Cys Phe Ala
 1               5
```